(12) United States Patent
Vidalin

(10) Patent No.: US 6,531,630 B2
(45) Date of Patent: Mar. 11, 2003

(54) BIMODAL ACETIC ACID MANUFACTURE

(76) Inventor: Kenneth Ebenes Vidalin, 750 World Trade Centre, 999 Canada Place, Vancouver, B.C. (CA), V6C 3E1

( * ) Notice: Subject to any disclaimer, the term of this patent is extended or adjusted under 35 U.S.C. 154(b) by 0 days.

(21) Appl. No.: 09/751,240

(22) Filed: Dec. 29, 2000

(65) Prior Publication Data

US 2002/0085963 A1 Jul. 4, 2002

(51) Int. Cl.$^7$ .......................... C07C 51/12; C07C 67/36; C07C 27/00
(52) U.S. Cl. .................. 562/519; 562/519; 560/206; 518/713; 518/702; 518/700
(58) Field of Search ................ 518/713, 702, 518/700; 560/206; 562/519; 422/148

(56) References Cited

U.S. PATENT DOCUMENTS

| | | | |
|---|---|---|---|
| 1,961,736 A | | 6/1934 | Carlin e al. |
| 2,622,089 A | | 12/1952 | Mayland |
| 2,727,064 A | | 12/1955 | Thomas et al. |
| 3,442,613 A | | 5/1969 | Grotz et al. |
| 3,769,329 A | * | 10/1973 | Paulik et al. |
| 3,859,230 A | | 1/1975 | Moe |
| 3,988,425 A | * | 10/1976 | Jockel et al. |
| 4,081,253 A | | 3/1978 | Marion |
| 4,110,359 A | | 8/1978 | Marion |
| 4,175,115 A | * | 11/1979 | Ball et al. |

(List continued on next page.)

FOREIGN PATENT DOCUMENTS

| | | |
|---|---|---|
| DE | 3712008 | 10/1988 |
| EP | 0845452 | 6/1996 |

OTHER PUBLICATIONS

U.S. patent application No. 09/751,240, Thiebaut et al.*
N. R. Udengaard, et al., "Sulfur passivated reforming process lowers syngas H2/CO ratio", Oil & Gas Journal, pp. 62–67, Mar. 9, 1992.
D.C. Hanson, et al., "The First Commercial Sulfur Passivated Reforming (SPARG) Plant," presented at Topsoe Seminar on Synthesis Gas Technologies, Houston, TX, USA, Nov. 1990.

(List continued on next page.)

*Primary Examiner*—Sreeni Padmanabhan
*Assistant Examiner*—Farhad Forohar
(74) *Attorney, Agent, or Firm*—Daniel N. Lundeen; Lundeen & Dickinson, LLP

(57) ABSTRACT

The converting of an existing methanol plant to make acetic acid is disclosed. The converted plant utilizes the steam reformer (10) to which (a) a hydrocarbon ,e.g., natural gas, or a lower alkanol, e.g., methanol, and (b) steam (water) are fed. Syngas is formed in the reformer (10). All or part of the syngas is processed to separate out carbon dioxide (24), carbon monoxide (30) and hydrogen (32), and the separated carbon dioxide (24) is fed either to the existing methanol synthesis loop (12) for methanol synthesis, or back into the feed to the reformer (10) to enhance carbon monoxide formation in the syngas (18). When a lower alkanol is fed to the reformer (10), the methanol synthesis loop (12) is shutdown and isolated from the rest of the plant. Any remaining syngas (38) not fed to the carbon dioxide separator (22) can be converted to methanol in the existing methanol synthesis loop (12) along with carbon dioxide (24) from the separator (22) and/or imported carbon dioxide (25), and hydrogen (35) from the separator (28). The separated carbon monoxide (30) is then reacted with the methanol (36) to produce acetic acid (40) or an acetic acid precursor by a conventional process. When the methanol synthesis loop (12) is shutdown, an imported source of methanol is used.

32 Claims, 7 Drawing Sheets

U.S. PATENT DOCUMENTS

| | | |
|---|---|---|
| 4,316,880 A | 2/1982 | Jockel et al. |
| 4,780,300 A * | 10/1988 | Yokoyama et al. |
| 4,833,171 A | 5/1989 | Sweeney |
| 4,891,950 A | 1/1990 | Seufert et al. |
| 4,994,603 A | 2/1991 | Mueller et al. |
| 5,104,419 A | 4/1992 | Funk |
| 5,155,261 A | 10/1992 | Marston et al. |
| 5,189,203 A | 2/1993 | Hansen et al. |
| 5,281,751 A | 1/1994 | Schreck et al. |
| 5,488,143 A | 1/1996 | Uhm et al. |
| 5,653,774 A | 8/1997 | Bhattacharyya et al. |
| 5,672,743 A | 9/1997 | Garland et al. |
| 5,728,871 A | 3/1998 | Joensen et al. |
| 5,767,165 A | 6/1998 | Steinberg et al. |
| 5,773,642 A | 6/1998 | Denis et al. |
| 5,817,869 A | 10/1998 | Hinnenkamp et al. |
| 5,840,969 A | 11/1998 | Joensen et al. |
| 5,855,815 A | 1/1999 | Park et al. |
| 5,877,347 A | 3/1999 | Ditzel et al. |
| 5,877,348 A | 3/1999 | Ditzel et al. |
| 5,883,289 A | 3/1999 | Denis et al. |
| 5,883,295 A | 3/1999 | Sunley et al. |
| 6,048,508 A | 4/2000 | Dummersdorf et al. |
| 6,171,574 B1 | 1/2001 | Juda et al. |
| 6,232,352 B1 | 5/2001 | Vidalin |
| 6,274,096 B1 | 8/2001 | Thiebaut et al. |
| 6,353,133 B1 | 3/2002 | Thieubaut et al. |

OTHER PUBLICATIONS

P.W. Evans, et al., "Low Steam/Gas Ratios in Reforming," Presented at the 1985 Ammonia Symposium Safety in Ammonia Plants and Related Facilities, American Institute of Chemical Engineers, Seattle, Washington, Aug. 1985 (AICHE Paper No. 51f).

* cited by examiner

BIMODAL ACETIC ACID MANUFACTURE

FIELD OF THE INVENTION

The present invention is directed generally to a process for making acetic acid from carbon monoxide and methanol, and more particularly to a bimodally operable plant wherein the carbon monoxide is obtained from syngas, or synthesis gas, made by reforming a hydrocarbon and synthesizing the methanol from the synthesis gas in a first mode of operation, or by reforming a lower alkanol and importing methanol for reaction with the carbon monoxide to form the acetic acid in a second mode of operation.

BACKGROUND OF THE INVENTION

The manufacture of acetic acid from carbon monoxide and methanol using a carbonylation catalyst is well known in the art. Representative references disclosing this and similar processes include U.S. Pat. No. 1,961,736 to Carlin et al (Tennessee Products); U.S. Pat. No. 3,769,329 to Paulik et al (Monsanto); U.S. Pat. No. 5,155,261 to Marston et al (Reilly Industries); U.S. Pat. No. 5,672,743 to Garland et al (BP Chemicals); U.S. Pat. No. 5,728,871 to Joensen et al (Haldor Topsoe); U.S. Pat. No. 5,773,642 289 to Denis et al (Acetex Chimie); U.S. Pat. No. 5,817,869 to Hinnenkamp et al (Quantum Chemical Corporation); U.S. Pat. No. 5,877,347 and U.S. Pat. No. 5,877,348 to Ditzel et al (BP Chemicals); U.S. Pat. No. 5,883,289 to Denis et al (Acetex Chimie); and U.S. Pat. No. 5,883,295 to Sunley et al (BP Chemicals), each of which is hereby incorporated herein by reference.

The primary raw materials for acetic acid manufacture are, of course, carbon monoxide and methanol. In the typical acetic acid plant, methanol is imported and carbon monoxide, because of difficulties associated with the transport and storage thereof, is generated in situ, usually by reforming natural gas or another hydrocarbon with steam and/or carbon dioxide. A significant expense for new acetic acid production capacity is the capital cost of the equipment necessary for the carbon monoxide generation. It would be extremely desirable if this capital cost could be largely eliminated or significantly reduced.

Market conditions, from time to time in various localities, can result in relatively low methanol prices (an oversupply) and/or high natural gas prices (a shortage) that can make methanol manufacture unprofitable. Operators of existing methanol manufacturing facilities can be faced with the decision of whether or not to continue the unprofitable manufacture of methanol in the hope that product prices will eventually rebound and/or raw material prices will drop to profitable levels. The present invention addresses a way of modifying an existing unprofitable methanol plant to make it more profitable when methanol prices are low and/or natural gas prices are high. The present invention also addresses a way of building a new plant with two modes of operation—one with a hydrocarbon feed and the other with an imported methanol feed.

As far as applicant is aware, there is no disclosure in the prior art for modifying existing methanol plants, including methanol/ammonia plants, to supply stoichiometric methanol and CO for manufacturing acetic acid, for example, that can be a more valuable product than methanol. Further, as far as applicant is aware, there is no disclosure in the prior art for modifying existing methanol plants, particularly the steam reformers thereof to reform either a hydrocarbon or a lower alkanol, e.g. methanol, using a hydrocarbon reforming catalyst with the optional presence of carbon dioxide, steam or both.

SUMMARY OF THE INVENTION

The present invention involves the discovery that the large capital costs associated with CO generation for a new acetic acid plant can be significantly reduced or largely eliminated by converting an existing methanol or methanol/ammonia plant to make acetic acid. The present invention is equally applicable to a new plant wherein the syngas producing portion of the plant accepts either a hydrocarbon feed, e.g., natural gas, or a lower alkanol feed, e.g., a methanol feed. The steam reformer is built or modified to accept either a natural gas feed or an imported methanol feed and to optionally have a carbon dioxide input, a steam input or both. The reformation takes place in the presence of a hydrocarbon reformation catalyst. Further, all or part of the syngas can be diverted from the methanol synthesis loop and supplied instead to a separator unit to recover $CO_2$, CO and hydrogen, which are advantageously used in various novel ways to produce acetic acid. When the steam reformer is operated with a lower alkanol feed, the methanol synthesis loop is shut down and isolated from the rest of the plant. In this case, all of the synthesis gas will be diverted from the methanol synthesis loop to the separation unit. The recovered $CO_2$ can be supplied to the reformer to enhance CO production, or to the methanol synthesis loop to make methanol. The recovered CO is usually supplied to the acetic acid reactor with the methanol to make the acetic acid. When a lower alkanol feed, e.g., methanol feed, is used for the reformer, methanol from an imported source is also supplied to the acetic acid reactor. The recovered hydrogen can be supplied to the methanol synthesis loop (when in use) for methanol production, used for the manufacture of ammonia or other products, burned as a fuel, or exported, since the hydrogen is normally produced in excess of the requirements for methanol synthesis in the present invention.

The carbon dioxide can be fed into a steam reformer to which (1) natural gas or methanol and (2) optionally steam (water) are fed. Syngas is formed in the reformer wherein both (1) the natural gas or methanol and (2) the carbon dioxide are reformed to produce syngas with a large proportion of carbon monoxide relative to reforming without added carbon dioxide. Alternatively or additionally, the $CO_2$ can be supplied to the methanol synthesis loop (when in operation), with additional CO from the synthesis gas and/or additional imported $CO_2$, for catalytic reaction with hydrogen to make methanol.

In the mode when the methanol synthesis loop is in operation, natural gas is preferably used as the hydrocarbon feed to the steam reformer. The syngas can be split into a first part and a second part. The first syngas part is converted to methanol in a conventional methanol synthesis loop that is operated at about half of the design capacity of the original plant since less syngas is supplied to it. The second syngas part can be processed to separate out carbon dioxide and carbon monoxide, and the separated carbon dioxide can be fed back into the feed to the reformer to enhance carbon monoxide formation, and/or fed to the methanol synthesis loop to make methanol. The separated carbon monoxide can then be reacted with the methanol to produce acetic acid or an acetic acid precursor by a conventional process.

In the mode wherein the methanol synthesis loop is shut down and isolated from the rest of the plant, imported lower alkanol, e.g., methanol, is used as a feed to the steam reformer and imported methanol is used as a feed to the acetic acid reactor. The syngas is processed to separate out carbon dioxide and carbon monoxide, and the separated carbon dioxide can be fed back into the feed to the reformer to enhance carbon monoxide formation. The separated carbon monoxide can then be reacted with the imported methanol to produce acetic acid or an acetic acid precursor by a conventional process.

In the mode wherein natural gas is used as a feed to the steam reformer, the method comprises the steps of: (a) diverting a portion of the syngas stream from at least one steam reformer to a separation unit; (b) operating the methanol synthesis loop with a feed comprising the remaining syngas stream to produce less methanol than the original methanol plant; (c) operating the separation unit to separate the diverted syngas into at least a carbon monoxide-rich stream and a hydrogen-rich stream, preferably wherein the quantity of hydrogen in the hydrogen-rich stream is greater than any net hydrogen production of the original methanol plant; and (d) reacting the carbon monoxide-rich stream from the separation unit with the methanol from the methanol synthesis loop to form the product, wherein the diversion of the syngas stream is balanced for the approximately stoichiometric production of the methanol from the methanol synthesis loop and the carbon monoxide-rich stream from the separation unit for conversion to the product.

In the mode wherein a lower alkanol, preferably methanol, is used as feed to the steam reformer, the method comprises the steps of: (a) feeding the syngas stream from at least one steam reformer to a separation unit; (b) isolating the methanol synthesis loop from the remainder of the plant; (c) operating the separation unit to separate the syngas into at least a carbon monoxide-rich stream and a hydrogen-rich stream; and (d) reacting the carbon monoxide-rich stream from the separation unit with the methanol from the imported source.

Preferably, the at least one steam reformer is built or modified to increase carbon monoxide production in the syngas stream. The steam reformer contains a hydrocarbon reformation catalyst and is used to reform a hydrocarbon, e.g., natural gas, or a lower alkanol ($C_1$-$C_3$ alcohol), e.g., methanol, to syngas. Alternatively, the steam reformer may utilize a methanol reformation catalyst to generate syngas when the plant is operating in the second mode with a methanol feed. The steam reformer is preferably modified to operate at a higher temperature. The syngas stream preferably comprises carbon dioxide, and the separation unit produces a carbon dioxide-rich stream that is preferably recycled to the at least one reformer to increase the carbon monoxide production.

The reaction step can include the direct catalytic reaction of methanol and carbon monoxide to form acetic acid as in the Mosanto-BP process, for example, or alternatively can comprise the intermediate formation of methyl formate and isomerization of the methyl formate to acetic acid, the intermediate reaction of a s mole of CO and two moles of methyl alcohol to form methyl acetate and hydrolysis of the methyl acetate to acetic acid and methanol, or the carbonylation of the methyl acetate to form acetic anhydride.

Separated hydrogen, which is generally produced in excess beyond that required for methanol synthesis in the present process, can also be reacted with nitrogen, in a conventional manner, to produce ammonia. Also, a portion of acetic acid that is produced can be reacted in a conventional manner with oxygen and ethylene to form vinyl acetate monomer. The nitrogen for the ammonia process (especially for any added ammonia capacity in a retrofit of an original methanol plant comprising an ammonia synthesis loop) and the oxygen for the vinyl acetate monomer process, can be obtained from a conventional air separation unit.

Broadly, the present invention provides, in one aspect, a method for converting an original methanol plant to a converted plant for manufacturing a product from carbon monoxide and methanol selected from the group consisting of acetic acid, acetic anhydride, methyl formate, methyl acetate and combinations thereof. The original methanol plant comprises at least one steam reformer for converting a hydrocarbon to a syngas stream containing hydrogen, carbon monoxide and carbon dioxide, and a methanol synthesis loop for converting hydrogen and carbon monoxide from the syngas stream to methanol. The method comprises the steps of: (1) providing the original methanol plant; (2) providing for selectively supplying a gaseous feed to the at least one steam reformer, wherein in a first mode the gaseous feed is a hydrocarbon and in a second mode the gaseous feed is a vaporized lower alkanol; (3) installing a vaporizer for vaporizing a lower alkanol from an imported source into the vaporized lower alkanol; (4) loading the at least one steam reformer with a hydrocarbon reformation catalyst for syngas generation; (5) installing a separation unit for separating all or part of the syngas stream into respective streams rich in carbon dioxide, carbon monoxide and hydrogen; (6) providing for diverting all or part of the syngas stream originally fed to the methanol synthesis loop to the separation unit; (7) providing for supplying at least a portion of the carbon dioxide-rich stream to the at least one steam reformer, to the methanol synthesis loop, or to a combination thereof; (8) installing isolation valves for isolating the methanol synthesis loop from the remainder of the converted plant when operated in the second mode; (9) installing a reactor for reacting carbon-monoxide and methanol to form the product; (10) providing for supplying at least a portion of the carbon monoxide-rich stream from the separation unit to the reactor; and (11) providing for supplying methanol to the reactor in the first mode from the methanol synthesis loop and in the second mode from an imported source.

The method for operating this converted plant comprises the steps of: (1) selecting between the first mode and the second mode of operation; and (2) operating the converted plant in the selected mode. The first mode of operation has at least the following steps (1) feeding the hydrocarbon to the at least one steam reformer, (2) operating the at least one steam reformer to generate syngas, (3) separating at least a portion of the syngas stream in the separation unit into respective streams rich in carbon dioxide, carbon monoxide and hydrogen, (4) operating the methanol synthesis loop with a feed comprising (a) carbon dioxide and (b) hydrogen, and (5) reacting at least a portion of the carbon monoxide-rich stream from the separation unit with methanol from the methanol synthesis loop to form the product. The second mode of operation has at least the following steps (1) vaporizing the lower alkanol, preferably methanol, (2) feeding the vaporized lower alkanol to the at least one steam reformer, (3) operating the at least one steam reformer to generate syngas, (4) separating all or part of the syngas stream in the separation unit into respective streams rich in carbon dioxide, carbon monoxide and hydrogen, (5) isolating the methanol synthesis loop from the remainder of the converted plant, and (6) reacting at least a portion of the carbon monoxide-rich stream from the separation unit with methanol from an imported source to form the product. Preferably, the product is acetic acid.

When the first mode is selected, the feed to the methanol synthesis loop can include imported carbon dioxide and/or a portion of the synthesis gas. Preferably, essentially all of the syngas stream is supplied to the separation step. The hydrogen supplied to the methanol synthesis loop is preferably provided by supplying at least a portion of the hydrogen-rich stream to the methanol synthesis loop. The amount of the hydrogen-rich stream is generally in excess of the stoichiometric hydrogen required by the methanol synthesis loop. Preferably, essentially all of the carbon dioxide-rich stream is supplied to the synthesis loop.

In either mode, essentially all of the carbon monoxide-rich stream is preferably supplied to the reaction step. The at least one steam reformer preferably has a second feed comprising a carbon dioxide-rich stream. This may be an imported stream or recycled from the separation unit. The carbon dioxide is converted to carbon monoxide in the reformer. The carbon dioxide-rich stream may be a mixed CO/carbon dioxide stream, for example, in a 1:2 to 2:1 molar ratio.

An imported carbon dioxide-rich stream can be supplied to the methanol synthesis loop (only in the first mode) or to the separation unit, but as noted above is preferably supplied to the reformer for conversion of the carbon dioxide to CO. In addition or alternatively, steam is fed to the at least one steam reformer.

In a preferred embodiment wherein the first mode is selected, the method for operating the modified or retrofitted plant comprises (1) supplying a major portion of the syngas stream to the separation unit for separating the syngas stream into respective streams rich in carbon dioxide, carbon monoxide and hydrogen, (2) operating the methanol synthesis loop with a feed comprising the carbon dioxide-rich stream from the separation unit, a minor portion of the syngas stream, and an additional source of carbon dioxide to produce a methanol stream, and (3) reacting the carbon monoxide-rich stream from the separation unit with the methanol stream from the methanol synthesis loop to form the product.

In another preferred embodiment wherein the first mode is selected, the method for operating the converted plant comprises (1) supplying the syngas stream to a separation unit for separating the syngas stream into respective streams rich in carbon dioxide, carbon monoxide and hydrogen, (2) operating the methanol synthesis loop with a feed comprising the carbon-dioxide-rich stream from the separation unit, a portion of the hydrogen-rich stream from the separation unit, a minor portion of the syngas stream, and carbon dioxide from an additional source, to produce a methanol stream, and (3) reacting the carbon monoxide-rich stream from the separation unit with the methanol stream from the methanol synthesis loop in essentially stoichiometric proportions to form the product.

In another aspect, the present invention provides a process for making hydrogen and a product selected from the group consisting of acetic acid, acetic anhydride, methyl formate, methyl acetate and combinations thereof. The process comprising the steps of: (1) reforming a hydrocarbon in a first mode or a lower alkanol in a second mode with steam using a hydrocarbon reformation catalyst to form a syngas containing hydrogen, carbon monoxide, and carbon dioxide; (2) recovering heat from the syngas to form a cooled syngas stream; (3) compressing the cooled syngas stream to a separation pressure; (4) separating at least a portion of the compressed syngas in a separation unit into a carbon dioxide-rich stream, a carbon monoxide-rich and a hydrogen-rich stream; (5) providing a methanol stream, wherein in the first mode the methanol stream is provided by operating a methanol synthesis loop to react hydrogen with carbon dioxide to form methanol, and in the second mode the methanol stream is provided from an imported source and the methanol synthesis loop is isolated from the remainder of the process; and (6) reacting the carbon monoxide-rich stream from the separation unit with the methanol stream in approximately stoichiometric proportions to form a product selected from the group consisting of acetic acid, acetic anhydride, methyl formate, methyl acetate and combinations thereof.

In one embodiment, wherein the first mode is selected, the sources of the hydrogen and carbon dioxide to the methanol synthesis loop are a first portion of the hydrogen from the separation unit and the carbon dioxide from the separation unit. Additional carbon dioxide from another source can be fed to the methanol synthesis loop.

With either mode selected, the reforming step is preferably conducted in the presence of carbon dioxide and the syngas produced by the reforming step has a molar R ratio (($H_2$—$CO_2$)/($CO+CO_2$)) from about 2.0 to about 2.9. Preferably, the carbon dioxide present in the reforming step is obtained by recycling the carbon dioxide-rich stream to the reforming step.

With the process in the first mode, the method may further include the steps of diverting a major portion of the compressed syngas to a separation unit; separating the syngas diverted to the separation unit into a carbon dioxide-rich stream, a carbon monoxide-rich stream and a hydrogen-rich stream; further compressing the remaining minor portion of the syngas to a methanol synthesis pressure higher than the separation pressure; operating a methanol synthesis loop to convert the hydrogen, carbon monoxide and carbon dioxide in the further compressed syngas into a methanol stream; and reacting the carbon monoxide-rich stream from the separation unit with the methanol stream from the methanol synthesis loop to form a product selected from the group consisting of acetic acid, acetic anhydride, methyl formate, methyl acetate and combinations thereof, wherein the diversion step is balanced to obtain approximately stoichiometric amounts of carbon monoxide and methanol.

The process preferably has a molar ratio of carbon dioxide to hydrocarbon comprising natural gas or methanol in feed to the reforming step from about 0.1 to 0.5. This feed preferably has a ratio of steam to natural gas or methanol from about 2 to 6. The methanol synthesis loop can be operated substantially below a total maximum combined design throughput of all methanol synthesis reactor(s) in the loop.

The process can further comprise the step of reacting the hydrogen in the hydrogen-rich stream with nitrogen in an ammonia synthesis reactor to make ammonia. The process can also comprise the step of separating air into a nitrogen stream and an oxygen stream and supplying the nitrogen stream to the ammonia synthesis reactor.

Regardless of whether the plant is a converted plant or a new plant, where the product comprises acetic acid, the reaction step preferably comprises reacting methanol, methyl formate, or a combination thereof in the presence of a reaction mixture comprising carbon monoxide, water, a solvent and a catalyst system comprising at least one halogenated promoter and at least one compound of rhodium, iridium or a combination thereof. The reaction mixture preferably has a water content up to 20 weight percent. Where the reaction step comprises simple carbonylation, the water content in the reaction mixture is more preferably from about 14 to about 15 weight percent. Where the reaction step comprises low-water carbonylation, the water content in the reaction mixture is more preferably from about 2 to about 8 weight percent. Where the reaction step comprises methyl formate isomerization or a combination of isomerization and methanol carbonylation, the reaction mixture more preferably contains a nonzero quantity of water up to 2 weight percent. The reaction step is preferably continuous.

Alternatively, the reaction step comprises the intermediate formation of methyl formate and isomerization of the methyl formate to acetic acid. Or, the reaction step may comprise the intermediate reaction of one mole of CO and two moles of methanol to form methyl acetate and hydrolysis of the methyl acetate to acetic acid and methanol.

Where the product comprises acetic acid or an acetic acid precursor which is converted to acetic acid, the process can further comprise the step of supplying the oxygen stream from the air separation unit to a vinyl acetate synthesis reactor, along with a portion of the acetic acid from the carbon monoxide-methanol reaction step, and ethylene, to produce a vinyl acetate monomer stream.

In another embodiment, the present invention provides a method for converting an original methanol plant into a converted plant for manufacturing a product from carbon monoxide and methanol selected from the group consisting of acetic acid, acetic anhydride, methyl formate, methyl acetate and combinations thereof. The original methanol plant comprises (1) at least one steam reformer for converting a hydrocarbon to a syngas stream containing hydrogen and carbon monoxide, (2) a heat recovery section for cooling the syngas stream, (3) a compression unit for compressing the syngas stream, and (4) a methanol synthesis loop for converting at least a portion of the hydrogen and carbon monoxide in the syngas stream to methanol. The method comprises the steps of: (1) providing the original methanol plant; (2) providing for selectively supplying to the at least one steam reformer in a first mode a hydrocarbon and in a second mode a vaporized lower alkanol; (3) installing a vaporizer for vaporizing a lower alkanol into the vaporized lower alkanol; (4) loading the at least one steam reformer with a hydrocarbon reformation catalyst for syngas generation; (5) installing a separation unit for separating the syngas fed thereto into respective streams rich in carbon dioxide, carbon monoxide and hydrogen; (6) installing isolation valves for isolating the methanol synthesis loop from the remainder of the converted plant when operated in the second mode; (7) modifying the flow of the syngas stream to allow diverting at least a portion of the syngas stream from the at least one reformer as a diverted syngas stream to the separation unit, wherein the separation unit is configured to separate the diverted syngas stream into at least a carbon monoxide-rich stream and a hydrogen-rich stream, preferably wherein the quantity of hydrogen in the hydrogen-rich stream is greater than any net hydrogen production of the original methanol plant; (8) modifying the operation of the methanol synthesis loop when in the first mode by changing the feed thereto to include at least the remaining syngas stream to produce less methanol than the original methanol plant; (9) installing a reactor for reacting the carbon monoxide-rich stream from the separation unit with methanol to form the product, wherein when in the first mode the diversion of the syngas stream is balanced for the approximately stoichiometric production of the methanol from the methanol synthesis loop and the carbon monoxide-rich stream from the separation unit for conversion to the product; (10) providing for supplying at least a portion of the carbon dioxide-rich stream to the at least one steam reformer, to the methanol synthesis loop, or to a combination thereof; (11) providing for supplying at least a portion of the carbon monoxide-rich stream from the separation unit; and (12) providing for selectively supplying methanol to the reactor in the first mode from the methanol synthesis loop and in the second mode from an imported source.

This method may further include the step of modifying the at least one steam reformer to increase carbon monoxide production in the syngas stream. Wherein the syngas stream comprises carbon dioxide and the separation unit produces a carbon dioxide-rich stream, this stream is preferably recycled to the at least one steam reformer to increase the carbon monoxide production. Wherein the syngas stream in the original plant has a molar ratio R $((H_2—CO_2)/(CO+CO_2))$ less than about 2.0 or greater than about 2.9, the syngas stream in the retrofitted plant preferably has an R ratio from about 2.0 to about 2.9.

In another aspect, the invention provides a method for retrofitting an original methanol plant into a converted plant for manufacturing a product from carbon monoxide and methanol selected from the group consisting of acetic acid, acetic anhydride, methyl formate, methyl acetate and combinations thereof. The original methanol plant has at least one steam reformer for converting a feed comprising hydrocarbon and steam essentially free of carbon dioxide into a syngas stream containing hydrogen and carbon monoxide, a heat recovery section for cooling the syngas stream, a compression unit for compressing the syngas stream, and a methanol synthesis loop for converting at least a portion of the hydrogen and carbon monoxide in the syngas stream to methanol. The method comprises the steps of: (1) providing the original methanol plant; (2) providing for selectively feeding to the at least one steam reformer a hydrocarbon in a first mode and a vaporized lower alkanol in a second mode; (3) installing a vaporizer for vaporizing the lower alkanol into the vaporized lower alkanol; (4) loading the at least one steam reformer with a hydrocarbon reformation catalyst for syngas generation; (5) installing a separation unit for separating syngas into a carbon dioxide-rich stream, carbon-monoxide-rich stream and a hydrogen-rich stream; (6) providing for diverting at least a portion of the syngas stream originally fed to the methanol synthesis loop to the separation unit; (7) providing for recycling at least a portion of the carbon dioxide-rich stream from the separation unit to the at least one steam reformer to increase the carbon monoxide formation relative to the original methanol plant and increase the molar ratio of carbon monoxide to hydrogen; (8) installing isolation valves for isolating the methanol synthesis loop from the remainder of the converted plant when operated in the second mode; (9) installing a reactor for reacting carbon-monoxide and methanol to form the product; (10) providing for supplying at least a portion of the carbon monoxide-rich stream from the separation unit to the reactor; and (11) providing for selectively supplying methanol to the reactor in the first mode from the methanol synthesis loop and in the second mode from an imported source. Further, when in the first mode, the diversion of the syngas stream is balanced for the approximately stoichiometric production of the methanol from the methanol synthesis loop using the remaining portion of the syngas stream and the carbon monoxide-rich stream from the separation unit for conversion to the product. In the second mode, the methanol synthesis loop is isolated from the remainder of the converted plant.

The modified steam reformer is preferably modified to operate at a higher temperature to enhance the carbon conversion to carbon monoxide. The separation unit can include a solvent absorber and stripper for carbon dioxide recovery, and a cryogenic distillation unit for carbon monoxide and hydrogen recovery.

The compression unit preferably has a three-stage compressor, and the syngas stream diversion preferably occurs between the second and third compression stages. The third compressor stage is preferably modified for operation at a lower throughput than the original methanol plant. Where the methanol synthesis loop of the original methanol plant includes a recycle loop compressor, the recycle loop compressor can also be modified for operation at a lower throughput.

The method can also comprise importing a stream of mixed CO/carbon dioxide, for example in a 1:2 to 2:1 molar ratio. The imported mixed CO/carbon dioxide stream can be supplied to the methanol synthesis loop or to the separation unit, but is preferably supplied to the reformer where the carbon dioxide therein is substantially converted to CO.

The method can further comprise the step of reacting the hydrogen in the hydrogen-rich stream with nitrogen to make ammonia. Where the original methanol plant produces a hydrogen-rich stream comprising a loop purge from the methanol synthesis loop that was reacted with nitrogen to make ammonia, the retrofitted plant can use the hydrogen-rich stream from the separation unit as a primary hydrogen source for the ammonia production. With the additional hydrogen available from the syngas, additional ammonia can be produced in the retrofitted plant relative to the original methanol plant.

The method can further comprise installing a vinyl acetate synthesis reactor for reacting a portion of the acetic acid with ethylene and oxygen to make vinyl acetate monomer. An air separation unit can be installed to make the oxygen for the vinyl acetate monomer unit, and the nitrogen produced from the air separation unit preferably matches the nitrogen required for the additional ammonia production.

In another embodiment, the present invention provides a method for converting an original methanol plant to a converted plant. The original methanol plant has at least (1) at least one steam reformer for converting a hydrocarbon to a syngas stream containing hydrogen, carbon monoxide, and carbon dioxide, and (2) a methanol synthesis loop for converting hydrogen and carbon monoxide from the syngas stream to methanol. The method comprises the steps of: (1) providing the original methanol plant; (2) providing for supplying a gaseous feed to the at least one steam reformer, wherein the gaseous feed is a vaporized lower alkanol; (3) installing a vaporizer for vaporizing a lower alkanol from an imported source into the vaporized lower alkanol; (4) loading the at least one steam reformer with a hydrocarbon reformation catalyst for syngas generation; (5) installing a separation unit for separating all or part of the syngas stream -into respective streams rich in carbon dioxide, carbon monoxide and hydrogen; (6) providing for diverting all of the syngas stream originally fed to the methanol synthesis loop to the separation unit; (7) providing for supplying at least a portion of the carbon dioxide-rich stream to the at least one steam reformer; (8) installing isolation valves for isolating the methanol synthesis loop from the remainder of the converted plant; (9) installing a reactor for reacting carbon-monoxide and methanol to form a product selected from the group consisting of acetic acid, acetic anhydride, methyl formate, methyl acetate and combinations thereof; (10) providing for supplying at least a portion of the carbon monoxide-rich stream from the separation unit to the reactor; and (11) providing for supplying a methanol stream from an imported source.

The present also provides a method for operating the converted plant. The method comprises the steps of: (1) vaporizing the lower alkanol, preferably methanol, (2) feeding the vaporized lower alkanol to the at least one steam reformer, (3) operating the at least one steam reformer to generate syngas, (4) separating all or part of the syngas stream in the separation unit into respective streams rich in carbon dioxide, carbon monoxide and hydrogen, (5) isolating the methanol synthesis loop from the remainder of the converted plant, and (6) reacting at least a portion of the carbon monoxide-rich stream from the separation unit with methanol from an imported source to form the product. The lower alkanol is preferably methanol. The product is preferably acetic acid.

DETAILED DESCRIPTION OF THE INVENTION

Figure 1:
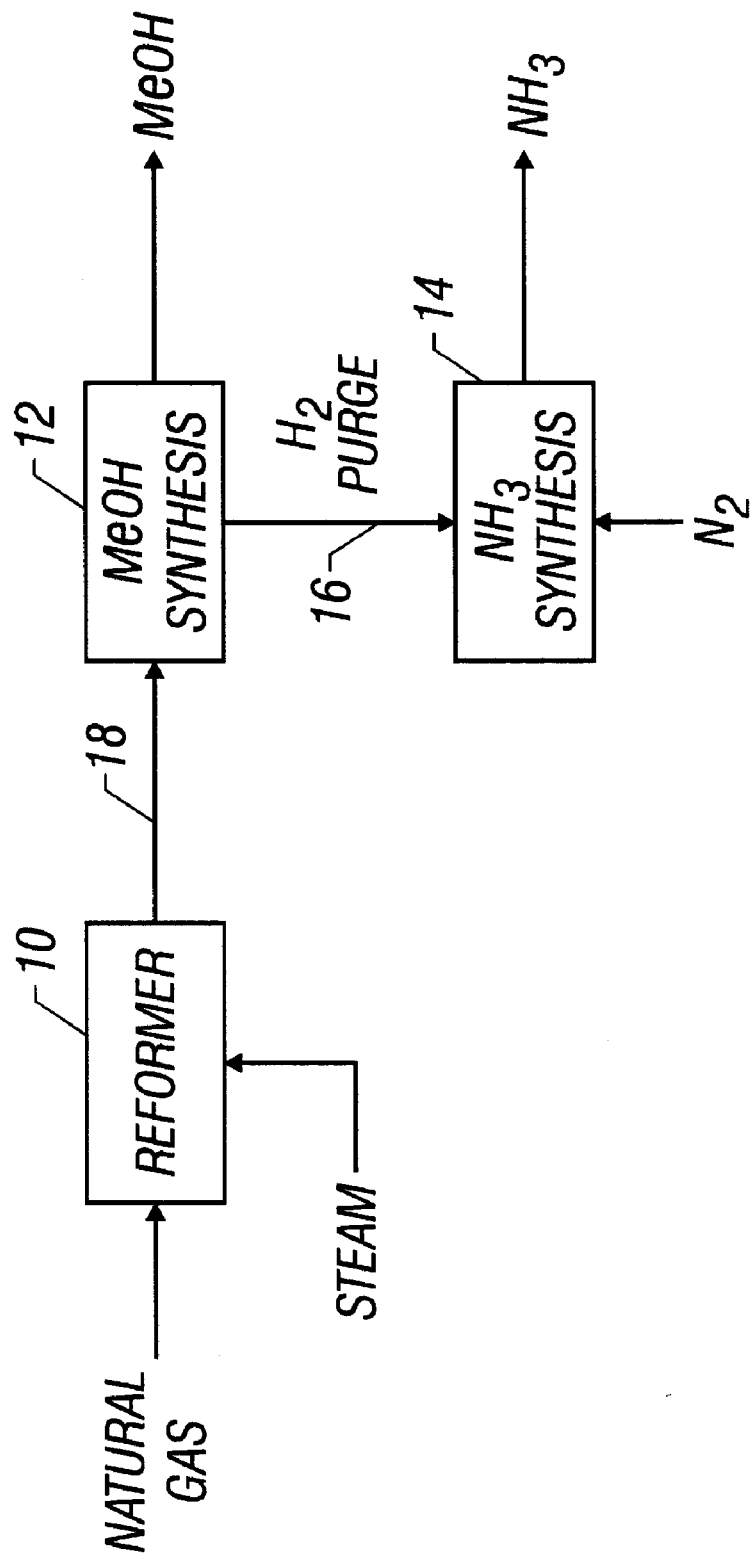
FIG. 1 (prior art) is an overall block flow diagram of a typical methanol/ammonia plant using hydrogen from the methanol synthesis loop purge to make ammonia, which can be converted according to the present invention for acetic acid manufacture.

With reference to FIG. 1, an original plant which can be converted according to one embodiment of the present invention has an existing conventional steam reformer unit 10, methanol (MeOH) synthesis unit 12 and preferably ammonia synthesis unit 14 wherein hydrogen for the ammonia synthesis unit 14 is taken as purge stream 16 from the methanol synthesis loop. The retrofit of the present invention is generally applicable to any plant that generates and uses synthesis gas to make methanol. As used in the present specification and claims, reference to "original plant" shall mean the plant as built and including any intervening modifications prior to the retrofit of the present invention.

The reformer unit 10 is typically a fired furnace containing parallel tube banks filled with conventional reforming catalyst such as alumina-supported nickel oxide, for example. The feed to the reformer(s) is any conventional reformer feed such as a lower hydrocarbon, typically naphtha or natural gas. The reformer can be a single-pass reformer or a two-stage reformer, or any other commercially available reformer, such as, for example, a KRES unit available from Kellogg, Brown & Root, as is known to those skilled in the art. The reformer effluent of the original methanol plant can contain any conventional $H_2$:CO ratio, but is normally close to 2.0 in plants making solely methanol, and substantially higher, e.g. 3.0 and above, in plants producing a separate hydrogen product or intermediate hydrogen-containing stream, e.g. for ammonia synthesis. The hydrogen-containing stream is typically obtained as purge stream 16 from the methanol synthesis unit 12 loop which is necessary to keep the level of hydrogen and inerts from building up in the synthesis gas recirculated through the methanol synthesis unit 12.

Figure 2:
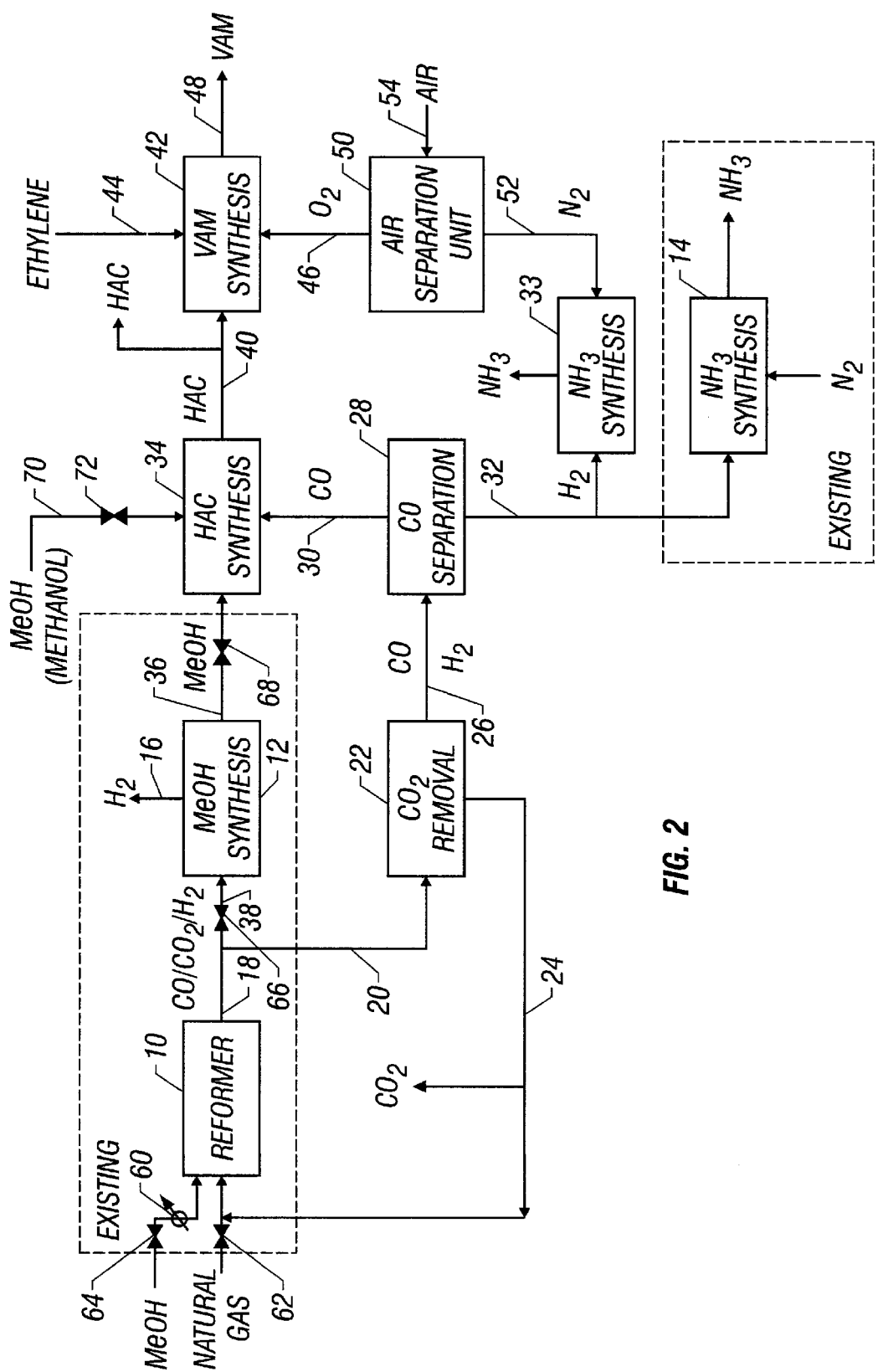
FIG. 2 is an overall block flow diagram of the plant of FIG. 1 after it has been converted according to the present invention to make acetic acid, vinyl acetate monomer and additional ammonia, plus allow for reforming either natural gas or methanol, and wherein the acetic acid reactor which can be supplied with methanol from the methanol synthesis loop or an imported source.

According to the present invention, the original plant of FIG. 1 is converted to produce acetic acid (HAC) using the existing reformer 10 and methanol synthesis unit 12, and keeping any ammonia synthesis unit 14, as shown in FIG. 2. The reformer 10 is fed either in the first mode a hydrocarbon feed, e.g., natural gas, or in the second mode a lower alkanol feed, e.g., methanol. A methanol feed would be used over natural gas when economics dictate. Valves 62 and 64 control which feed is used. The methanol is preferably vaporized in vaporizer 60 prior to being fed to reformer 10. Thus, the retrofitted plant in FIG. 2 can operate in a first mode using a natural gas feed or in a second mode using a methanol feed. In the second mode, the methanol synthesis unit 12 is shutdown and isolated from the remainder of the plant using isolation valves 66 and 68.

Depending in which mode the plant is operating, all or a portion of the effluent 18 from the reformer 10 is diverted from the methanol synthesis unit 12 via line 20 to a new $CO_2$ removal unit 22. The $CO_2$ removal unit 22 separates the stream from line 20 into a $CO_2$-rich stream 24 and a $CO_2$-lean stream 26 using conventional $CO_2$ separation equipment and methodology such as, for example, absorption-stripping with a solvent such as water, methanol, generally aqueous alkanolamines such as ethanolamine, diethanolamine, methyldiethanolamine and the like, aqueous alkali carbonates such as sodium and potassium carbonates, and the like. Such $CO_2$ absorption-stripping processes are commercially available under the trade designations Girbotol, Sulfinol, Rectisol, Purisol, Fluor, BASF (aMDEA) and the like.

The $CO_2$ recovered from the $CO_2$ removal unit 22 or from another source can be supplied to the reformer 10. Increasing the $CO_2$ in the feed to the reformer 10 increases the CO content of the effluent 18. Analogous to steam reforming where a hydrocarbon reacts with steam to form synthesis gas, the reaction of the hydrocarbon or lower alkanol with carbon dioxide is often called $CO_2$ reforming. As the carbon dioxide content of the reformer feed is increased, the share of the carbon in the carbon monoxide in the product synthesis gas 18 that is supplied from the carbon dioxide increases in relative proportion and the share originating from the hydrocarbon or lower alkanol decreases. So, for a given CO production rate, the hydrocarbon feed gas or lower alkanol feed requirement is reduced. During the early stage of reforming, heavier hydrocarbons are converted to methane:

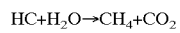

$$HC + H_2O \rightarrow CH_4 + CO_2$$

The main steam and $CO_2$ reforming reactions convert methane or methanol to hydrogen and carbon monoxide. For methane, the reforming reactions are:

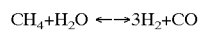

$$CH_4 + H_2O \leftrightarrow 3H_2 + CO$$

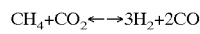

$$CH_4 + CO_2 \leftrightarrow 3H_2 + 2CO$$

The shift reaction converts carbon monoxide to carbon dioxide and more hydrogen:

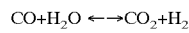

$$CO + H_2O \leftrightarrow CO_2 + H_2$$

The conversion of the heavier hydrocarbons goes to completion. The steam reforming, $CO_2$ reforming, and shift reaction are equilibrium-restricted. The overall reaction is strongly endothermic. The reformer 10 can, if desired, be modified for additional heat input for supplemental $CO_2$ reforming and additional heat recovery. The effluent 18 from the modified reformer 10 has a molar ratio of hydrogen minus $CO_2$ to CO plus $CO_2$ (referred to in the present specification and claims as the "R ratio" $(H_2-CO_2)/(CO+CO_2)$), which can be optimized for methanol synthesis, preferably within the range from 2.0 to 2.9. The possibility of optimizing the R ratio arises from the discovery that the hydrogen for the ammonia synthesis no longer needs to be obtained as the methanol purge stream 16, but can instead be recovered from the syngas diverted via line 20 as discussed in more detail below.

The $CO_2$-lean stream 26 contains primarily CO and hydrogen and can be separated in CO separation unit 28 into a CO-rich stream 30 and a hydrogen-rich stream 32. The separation unit 28 can comprise any equipment and/or methodologies for separating the CO/hydrogen mixture into relatively pure CO and hydrogen streams, such as, for example, semi-permeable membranes, cryogenic fractionation, or the like. Cryogenic fractional distillation is preferred, and can include simple partial condensation without any columns, partial condensation with columns, optionally with a pressure swing absorption (PSA) unit and a hydrogen recycle compressor, or methane wash. Normally, partial condensation with columns is sufficient for obtaining CO and hydrogen of sufficient purity for acetic acid and ammonia production, respectively, keeping equipment and operating costs to a minimum, although the PSA unit and hydrogen recycle compressor can be added for increasing the hydrogen purity and CO production rate. For acetic acid manufacture, the CO stream 30 preferably contains less than 1000 ppm hydrogen and less than 2 mole percent nitrogen plus methane. For ammonia production, the hydrogen stream 32 which is sent to a nitrogen wash unit (not shown) preferably contains at least 80 mol % hydrogen, more preferably at least 95 mol % hydrogen.

A portion of the hydrogen stream 32 is supplied to the existing ammonia synthesis unit 14 in place of the methanol loop purge stream 16. The quantity of hydrogen produced in the stream 32 is generally much larger than the amount previously supplied via line 16. This is due in large part to the fact that less methanol is made in the retrofitted plant, and thus less hydrogen is consumed for methanol synthesis. The additional hydrogen capacity can be used as a fuel supply, or as a raw hydrogen source for another process, such as, for example, increased ammonia conversion. Additional ammonia can be made by supplying a portion of the additional hydrogen to the existing ammonia synthesis reactor 14 where the ammonia conversion capacity can be increased, and/or by installing additional ammonia synthesis unit 33. The increased ammonia capacity can be complemented by the presence of existing ammonia handling, storage and transport facilities which may be able to accommodate the additional ammonia capacity with little or no modification.

The methanol synthesis unit 12 is a conventional methanol conversion unit such as, for example, an ICI reactor. The methanol synthesis unit 12 of the retrofitted plant shown in FIG. 2 can be isolated from the remainder of the plant using valves 66 and 68 when the plant is operated in the second mode. The methanol synthesis unit 12 is used when the plant is operating in the first mode and is essentially the same as in the original plant prior to the retrofit, except that the quantity of methanol produced is substantially lower, preferably about half of that of the original plant. Concomitantly, the loop recycle compressor (not shown) is operated at a lower capacity and the purge stream 16 is considerably reduced in quantity. As mentioned above, the purge stream 16 is no longer needed for supplying the hydrogen to the ammonia converter 14, since this is now supplied in the converted plant from the hydrogen stream 32 separated directly from the portion of the reformer 10 effluent 18 diverted from the feed to the methanol synthesis unit 12 via line 20. If desired, the purge stream 16 can now be used for fuel and/or as a hydrogen source for hydrodesulfurization of the feed to the reformer 10. Since there is no longer any need to pass the excess hydrogen through the methanol synthesis unit 12 for use in the ammonia unit 14, the feed to the methanol synthesis unit 12, i.e. the effluent 18, can be compositionally optimized for more efficient methanol conversion, as described above. It can also be desirable to modify the methanol synthesis unit 12, if desired during the retrofit, to include any other modifications which are not present in the original plant but have become conventional and have been developed for methanol synthesis loops since the construction of the original plant and have not previously been incorporated therein.

When the plant is operated in the first mode, the amount of syngas in the effluent 18 from the reformer 10 which is diverted to $CO_2/CO/H_2$ separation is preferably balanced to provide a stoichiometric ratio of methanol and CO to produce acetic acid therefrom in acetic acid synthesis unit 34. Preferably, the ratio of CO in line 30 and methanol in line 36 is about equal or the methanol is produced at a 10-20% molar excess, e.g. a molar ratio from 1.0 to about 1.2. To produce this ratio of methanol and CO, a relatively larger quantity (total kg/hr) of the effluent 18 is diverted into line 20, and the remaining minor portion is fed in line 38 to the methanol synthesis unit 12.

When the plant is operated in the second mode, methanol is fed to the acetic acid synthesis unit 34 via line 70 and valve 72 from an imported source.

The acetic acid synthesis unit 34 employs conventional acetic acid manufacturing equipment and methodology well known and/or commercially available to those skilled in the art, such as, for example, from one or more of the acetic acid manufacturing patents mentioned above. For example, a conventional BP/Monsanto process can be employed, or an improved BP/Monsanto process employing BP-Cativa technology (iridium catalyst), Celanese low water technology (rhodium-lithium acetate catalyst), Millenium low water technology (rhodium-phosphor oxides catalyst), Acetex technology (rhodium-iridium catalyst) and/or dual process methanol carbonylation-methyl formate isomerization. The reaction generally comprises reacting methanol, methyl formate, or a combination thereof in the presence of a reaction mixture comprising carbon monoxide, water, a solvent and a catalyst system comprising at least one halogenated promoter and at least one compound of rhodium, iridium or a combination thereof. The reaction mixture preferably has a water content up to 20 weight percent. Where the reaction comprises simple carbonylation, the water content in the reaction mixture is preferably from about 14 to about 15 weight percent. Where the reaction comprises low-water carbonylation, the water content in the reaction mixture is preferably from about 2 to about 8 weight percent. Where the reaction comprises methyl formate isomerization or a combination of isomerization and methanol carbonylation, the reaction mixture preferably contains a nonzero quantity of water up to 2 weight percent. The reaction is typically continuous. An acetic acid product is obtained via line 40.

If desired, a portion of the acetic acid from line 40 can be fed to a conventional vinyl acetate monomer synthesis unit 42 where it is reacted with ethylene via line 44 and oxygen via line 46 to obtain monomer product stream 48. The oxygen in line 46 can be obtained, for example, using a conventional (preferably cryogenic) air separation unit 50 which also produces a nitrogen stream 52 corresponding to the amount of air from line 54 needed for the oxygen in line 46. The amount of air separated can be matched to produce the nitrogen required via line 52 for the additional ammonia capacity added by ammonia synthesis unit 33 as mentioned above.

Figure 5:
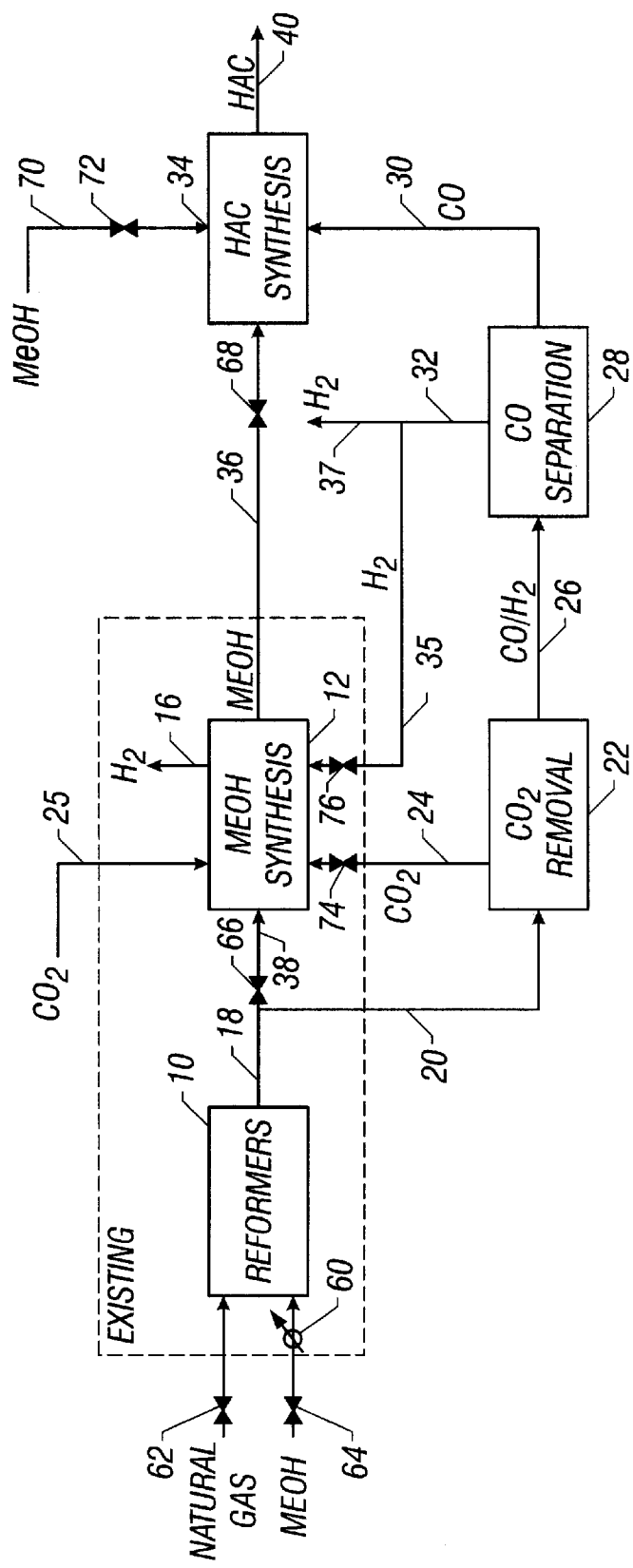
FIG. 5 is an overall block flow diagram of the plant of FIG. 1 after it has been converted according to an alternate embodiment of the present invention wherein the reformer may be supplied with either natural gas or methanol, a portion of the syngas stream is diverted to separation, the isolateable MeOH synthesis loop can be supplied with hydrogen and $CO_2$ recovered from the separation, a remaining portion of the syngas and additional imported $CO_2$, and the acetic acid reactor which can be supplied with methanol from the methanol synthesis loop or an imported source.

In the alternate embodiment shown in FIG. 5, the CO available for acetic acid manufacture is increased by diverting a much larger portion of the syngas from line 18 via line 20 to the $CO_2$ removal unit 22, than in the embodiment of FIG. 2. This increases the requirement for CO needed for the methanol synthesis unit 12. However, the CO requirement for the methanol synthesis unit 12 can also be met by supplying $CO_2$, although the hydrogen required for methanol synthesis with $CO_2$ is higher. The $CO_2$ stream 24 from the $CO_2$ removal unit 22 is thus supplied to methanol synthesis unit 12 via valve 74 instead of reformer 10 as in the FIG. 2 embodiment. Additional CO or $CO_2$, or a mixture of $CO/CO_2$, as needed for the methanol synthesis 12 can be supplied from another source (not shown) via line 25. It is preferred to import $CO_2$ instead of CO because $CO_2$ is usually easier to produce and transport than CO, and it is also less toxic. Some of the hydrogen obtained in line 32 from the CO separation unit 28 can be supplied via line 35 to the methanol synthesis unit 12. Since the amount of hydrogen in line 32 and valve 76 is generally greater than the amount of hydrogen required for methanol synthesis unit 12, even when using $CO_2$ as a feedstock in place of CO, the excess hydrogen via line 37 can be exported for another use, such as, for example, ammonia synthesis or combustion as a fuel gas.

The embodiment of FIG. 5 can have advantages over that of FIG. 2 in that the retrofit does not require as many modifications of the reformers 10, and the methanol synthesis unit 12 can be operated at essentially design capacity when the plant is operated in the first mode without significantly changing any stream compositions in the methanol synthesis unit 12. Furthermore, the embodiment of FIG. 5 can be operated without excess methanol production, while at the same time producing hydrogen via line 37 for export.

In the second mode of operation, the methanol synthesis unit 12 is isolated from the remainder of the plant using valves 74 and 76 in addition to valves 66 and 68.

Figure 6:
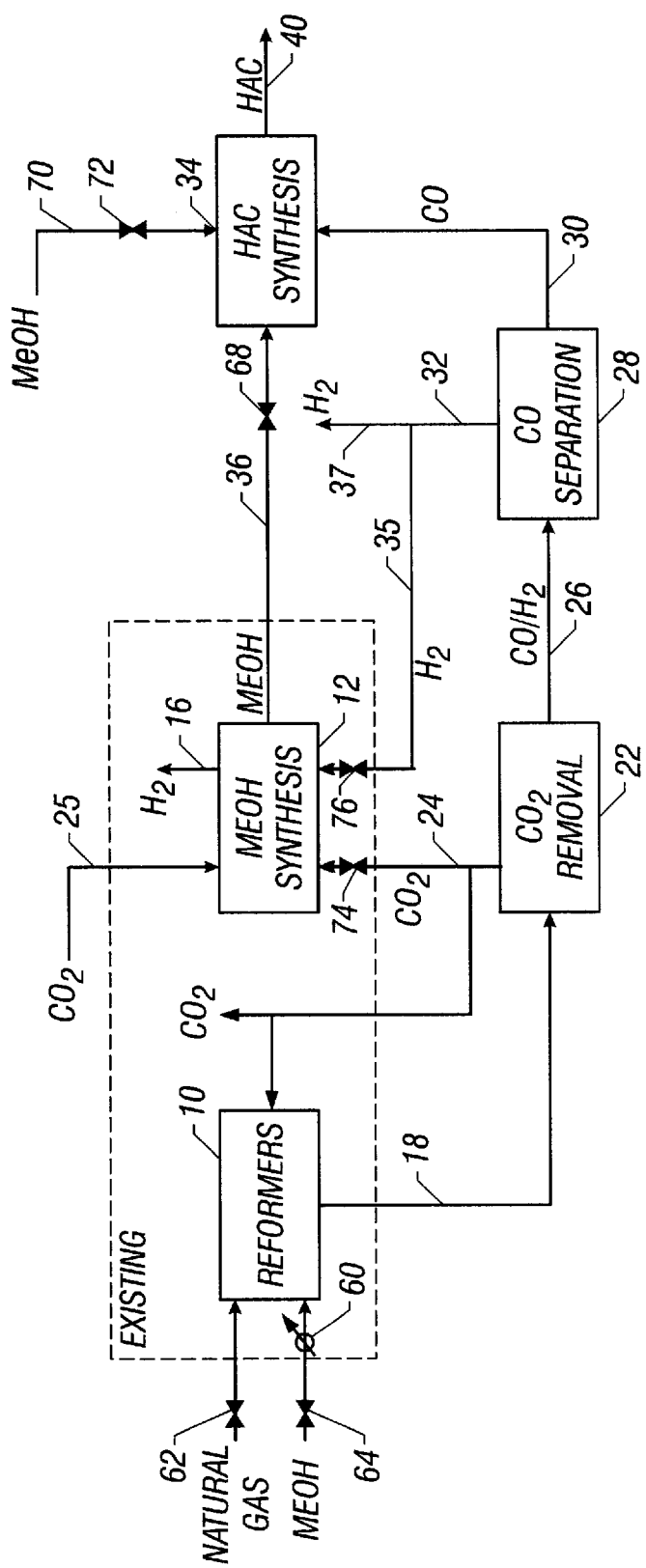
FIG. 6 is an overall block flow diagram of the plant of FIG. 1 after it has been converted according to another alternate embodiment of the present invention wherein the reformer may be supplied with either natural gas or methanol, all of the syngas stream is diverted to separation, the isolatable MeOH synthesis loop can be supplied with hydrogen and $CO_2$ recovered from the separation and additional imported $CO_2$, and the acetic acid reactor which can be supplied with methanol from the methanol synthesis loop or an imported source.

The embodiment of FIG. 6 is similar to FIG. 5 except that there is no syngas supplied to the methanol synthesis unit 12, and it is instead supplied in its entirety to the $CO_2$ removal unit 22. Therefore, the is no corresponding line 38 and valve 66. This has the further advantage of maximizing CO and acetic acid production with slightly higher $CO_2$ import requirements and slightly less hydrogen production via line 37.

Figure 3:
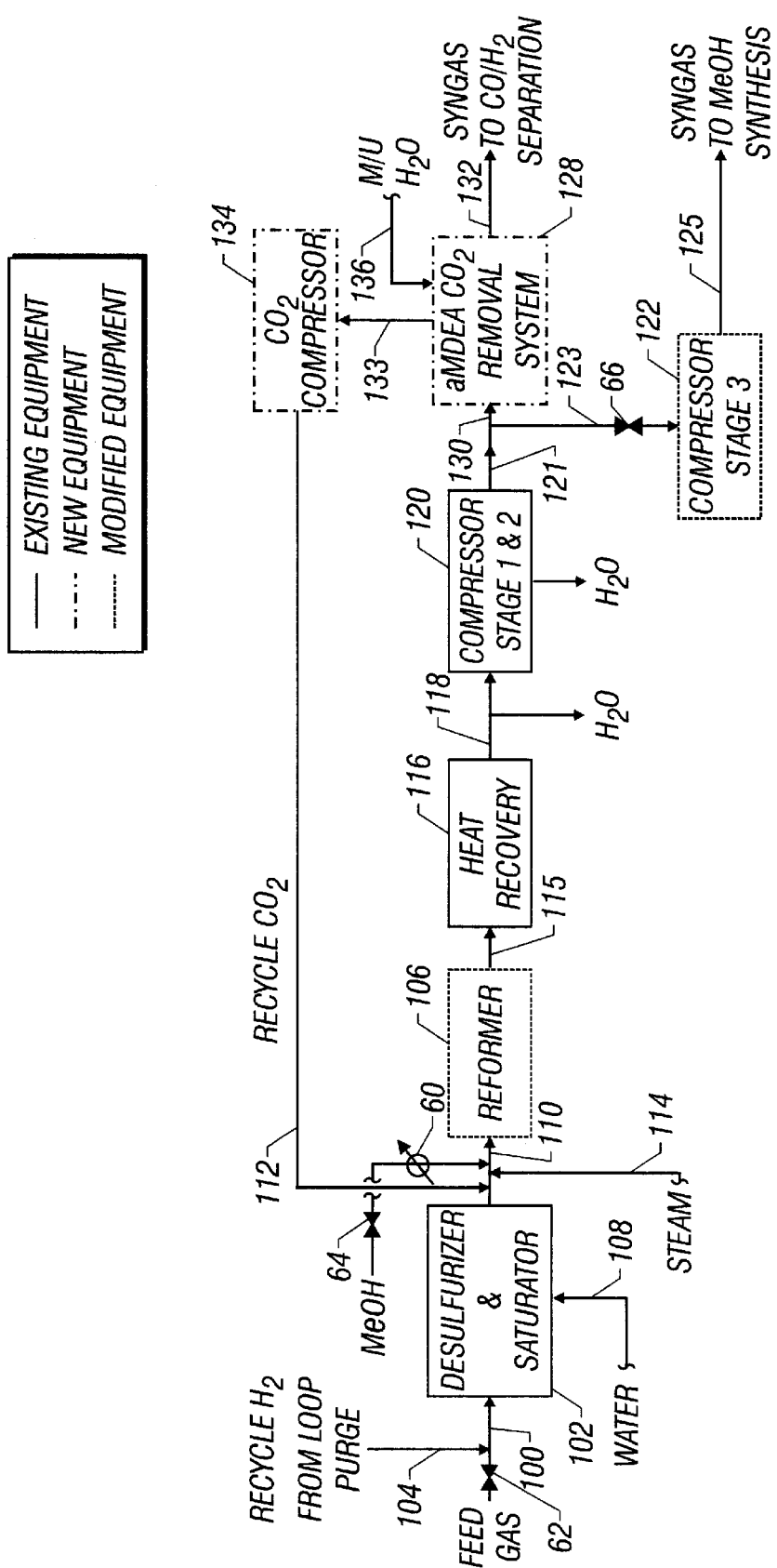
FIG. 3 is a simplified schematic process flow diagram of the front end of the plant of FIG. 2 showing the synthesis gas production and $CO_2$ recycle in the converted plant wherein existing equipment is shown as a solid line, new equipment as a dash-dot-dash line, and modified equipment as a dotted line.
Figure 4:
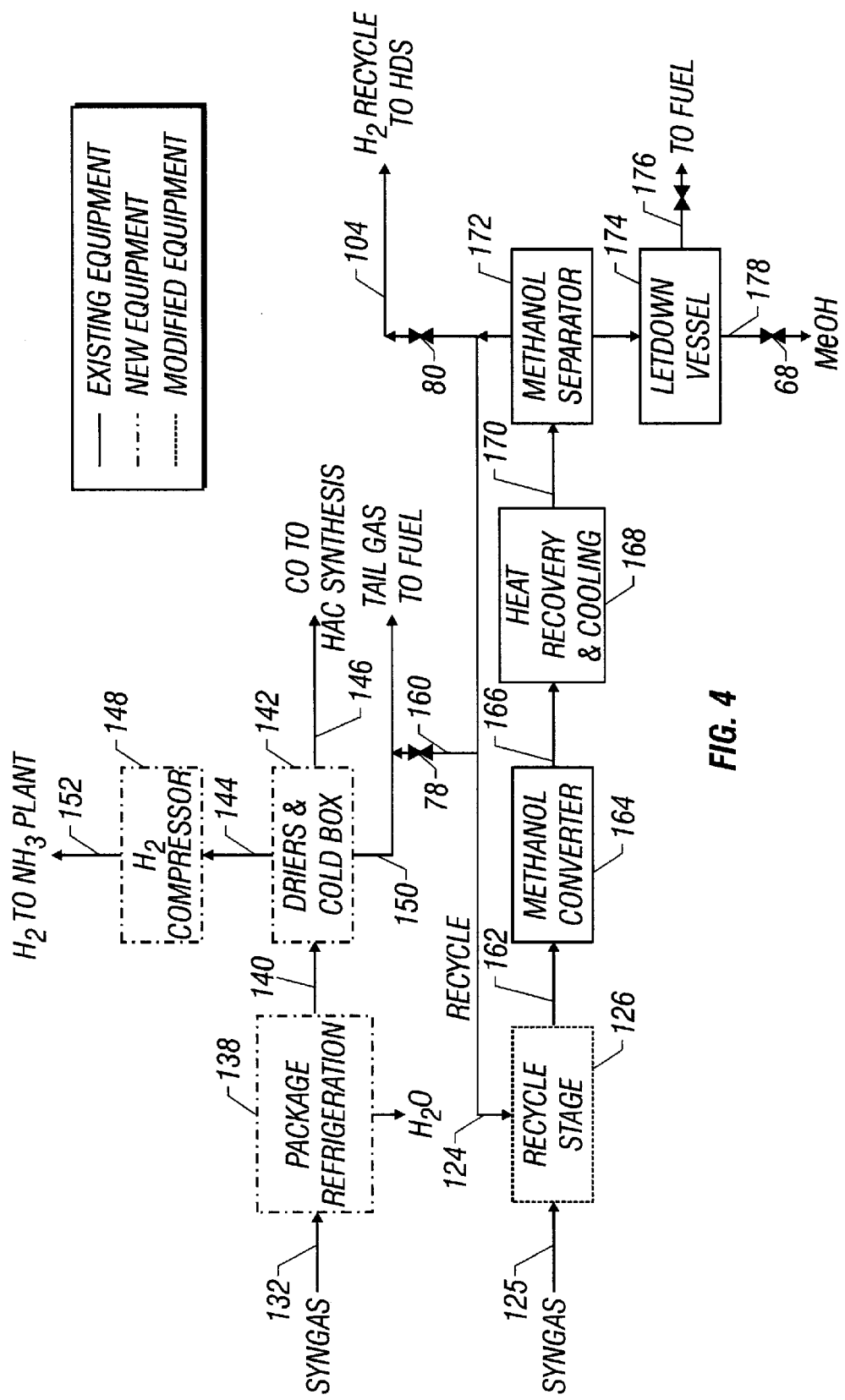
FIG. 4 is a simplified schematic process flow diagram of a portion of the plant of FIG. 2 showing the $CO/H_2$ separation and the isolateable methanol synthesis loop in the converted plant wherein existing equipment is shown as a solid line, new equipment as a dash-dot-dash line, and modified equipment as a dotted line.

The original plant is retrofitted in accordance with FIGS. 3 and 4 to produce methanol and CO to make acetic acid, and hydrogen which is used to make ammonia. The retrofit of the existing methanol plant includes its reconfiguration for operation in the first mode to produce methanol and CO in stoichiometric ratio for acetic acid manufacture while still producing hydrogen at least sufficient for existing ammonia synthesis. The existing reformer 106 is modified to add a new induced draft fan (not shown) and larger steam superheat, mixed feed and feed coils (not shown). The existing third stage synthesis gas compressor 122 is modified for a lower throughput by replacing the inner bundle including rotor and diaphragms. The existing synthesis gas recirculation compressor 126 is similarly modified for a lower flow rate by replacing the inner bundle including rotor and diaphragms. A new aMDEA $CO_2$ removal unit 128, a new package refrigeration unit 138, a new cold box unit 142 including driers and CO compressor, a new $CO_2$ compressor 134 to recycle $CO_2$ to the reformer 106 and new hydrogen compressors 148 to supply hydrogen to the existing ammonia plant (not shown) and a new ammonia plant (not shown) are added. Prior to and/or during the retrofit (at least while the existing equipment is operational, before shutdown construction), the methanol plant can be operated at a reduced rate, bypassing a portion of the synthesis gas from the discharge of the synthesis gas compressor 122 directly to the existing ammonia plant.

Advantages of the retrofit compared to a completely new CO/MeOH plant are the use of existing units and equipment, such as desulfurization, reforming including waste heat recovery, synthesis gas compressor and circulator, etc. Additional advantage is provided by the use of the existing offsite and infrastructure such as steam generation, water treatment, cooling water system, control room and product loading facilities.

Referring to FIG. 3, there is shown a block flow diagram for an embodiment of the retrofitted plant. In the first mode where natural gas is supplied to the reformer 106, natural gas is supplied in line 100 via valve 62 to desulfurizer/saturator unit 102. The existing sulfur removal system is used to remove any $H_2S$ and organic sulfur from the process feed gas. This gas is mixed with a recycle stream 104 of hydrogen-rich synthesis gas, and is heated in the desulfurizer heat exchanger (not shown) and in the convection section 116 of the reformer 106. The heated gas enters the desulfurizer unit 102 where organic sulfur compounds are first hydrogenated to hydrogen sulfide over a bed of nickel/molybdenum catalyst (not shown). Below the NiMo catalyst is a bed of zinc oxide adsorbent (not shown) in which the hydrogen sulfide is reacted to form zinc sulfide. The desulfurized feed is passed through the existing saturator where the gas is saturated with water from line 108 to reduce the process steam requirement.

In the second mode, methanol is fed to reformer 106 via valve 64 and vaporized in vaporizer 60. The gas exiting the saturator in line 110 or the vaporizer 60, depending on the mode of operation, is mixed with recycle carbon dioxide in line 112 and medium-pressure steam from line 114 so that the mixed gas has about 3 moles of equivalent steam per mole of carbon, where equivalent steam is calculated as moles of steam plus 0.6 times moles of carbon dioxide.

The use of vaporized methanol as a feed gas is a modification of the existing operation of reformer 106. This provides novel and added operational flexibility to the converted plant to produce value added products such as acetic acid based on the relative economics of natural gas procurement and methanol production compared to methanol procurement.

Addition of $CO_2$ to the feed gas is another modification of the existing operation of the reformer 106. This produces more CO and balances the synthesis gas composition in effluent stream 115 for more efficient methanol production as described above. The mixed feed is preheated in the modified mixed feed coils (not shown) in the reformer 106.

The hot mixed feed is distributed to the reformer 106 catalyst tubes (not shown), passes down through the nickel reforming catalyst, and reacts to form hydrogen, CO and $CO_2$. The heat recovery unit 116 is a convection section of the reformer 106 and includes coils for the high pressure steam boiler, high pressure steam superheating (modified in the retrofitted plant), mixed feed preheating (modified in the retrofitted plant), feed gas preheating (modified in the retrofitted plant), and combustion air preheating. As mentioned above, modified coils are provided for steam superheating, mixed feed preheating and feed gas preheating services. The reformer 106 includes a new induced draft fan. The old induced draft fan is used as the forced draft fan in the retrofitted plant. The reformer effluent 115 is used to generate steam, preheat boiler feed water, and provide heat in the reboilers for the topping and refining columns in the existing exchangers (not shown).

The synthesis gas in line 118 is compressed in the first casing of the existing synthesis compressor (first and second stages 120) without modification. The gas in discharge line 121 is then split so that a major portion thereof goes to the $CO/H_2$ production via line 130 and the rest is sent via line 123 and valve 66 to the second casing (third stage compressor 122 supplying syngas to line 125 for MeOH synthesis). The third compressor stage 122 of the synthesis gas compressor handles, for example, less than 50% of the flow of the original plant. This casing is modified with a new inner bundle including rotor and diaphragms. The gas is then cooled in the original third inter-stage cooler (not shown) arid water is separated in the original inter-stage separator (not shown). The make-up gas in line 125 is then mixed with recycle gas from line 124 (see FIG. 4) and compressed in recycle circulator 126. Since the circulator 126 will be handling significantly less than the original flow, the circulator 126 will require a new inner bundle including rotor and diaphragms.

A major portion of the gas from the second stage of the synthesis gas compressor 120 is sent via line 130 to a new aMDEA $CO_2$ removal system 128. A single-stage aMDEA system is available for licensed from BASF in which the circulating solution is about 40 wt % aMDEA, designed to reduce the carbon dioxide content in the gas stream 130 from about 9.7 vol % to 100 ppmv, on a dry basis, in line 132. The absorber (not shown) is operated, for example, at 35° to 40° C. and about 39.5 bars (absolute). The absorber overhead gas (not shown) enters a knockout drum (not shown) for separation of any entrained solution. The rich solution from the absorber bottom passes through a hydraulic turbine (not shown) for power recovery. The turbine produces power to help drive one of the lean solution pumps (not shown). The solution then enters a stripper (not shown) designed in three sections: a contact cooler on top, a low-pressure (LP) flash section in the middle, and a stripper section in the bottom. The rich solution from the hydraulic turbine enters the LP flash section which promotes $CO_2$ flashing by pressure reduction. A semi-lean solution pump (not shown) pumps the solution from the bottom of the LP flash section through the lean/semi-lean solution exchanger (not shown) to the top of the stripper section. The exchanger recovers heat from the lean solution leaving the stripper section. The solution leaving the stripper section is reboiled by low-pressure steam in a $CO_2$ stripper steam reboiler (not shown). The carbon dioxide and steam from the LP flash section is cooled to 35° C. in the contact cooler section. This is accomplished by contact with cooling water. Cooled carbon dioxide having a purity of at least 99 vol % on a dry basis is sent via line 133 to new $CO_2$ compressor 134, a four-stage, motor-driven, integrally geared turbo compressor which discharges the $CO_2$ into line 112 for recycle to the reformer 106 upstream from the mixed feed coil as mentioned previously. The regenerated lean solution is cooled in the lean/semi-lean solution exchanger and then by cooling water. The cooled lean solution is pumped to the top section of the absorber, and a slipstream can be filtered to remove solids. Make-up water is added to the system via line 136.

The synthesis gas in line 132 is cooled in new package refrigeration unit 138 (see FIG. 4) which uses a screw compressor and ammonia as refrigerant. The chilled synthesis gas from the unit 138 is then passed via line 140 into driers/cold box unit 142 where it is dried and separated cryogenically into noncondensed hydrogen stream 144 and CO stream 146. The driers (not shown) are parallel beds packed with molecular sieve, one of which is on line while the other is being regenerated. In the driers, the moisture content of the gas is typically reduced below 0.5 ppmv and the carbon dioxide content is reduced below 1 ppmv. Each drier can normally operate 12 hours and regeneration with hot (about 288° C.) reject gas from the $CO/H_2$ plant and cooling takes about 6 hours, allowing 6 hours of stand-by.

The separation of CO and $H_2$ in the cold box employs a partial condensation process using two columns (not shown). The dried gas from the driers is cooled and partially liquefied in feed/effluent exchangers (not shown). The liquid is separated out, while the hydrogen product is superheated and expanded in a hydrogen expansion turbine (not shown). Cold gas from the turbine is re-heated in the feed/effluent exchangers and leaves the cryogenic unit via line 144. The liquid that was separated out, rich in CO, is flashed into a hydrogen reject column (not shown). Flash gas containing mostly hydrogen is taken from the top of the column, and re-heated in the feed/effluent exchangers to the same temperature and pressure as the gas from the turbine with which it is mixed in line 144 for supply to the hydrogen compressor 148.

Reboil for the hydrogen reject column is provided by condensing high pressure CO in a reboiler (not shown). The bottom product from the hydrogen reject column, now lean in hydrogen but containing excess methane, is flashed into a $CO/CH_4$ column (not shown) where $CH_4$ is separated from the CO and exits the column as a liquid bottoms product. The liquid methane is evaporated and heated to ambient in the feed/effluent exchangers and exits the unit 142 as fuel gas via line 150. The CO from the top of the $CO/CH_4$ column is heated in the feed/effluent exchangers and compressed in a CO compressor (not shown) into line 146. The CO compressor is also utilized in the heat pump cycle by cooling CO in one of the feed/effluent exchangers, condensing in the reboilers for the hydrogen reject and $CO/CH_4$ columns and subcooling in another one of the feed/effluent exchangers. Subcooled liquid CO is used as reflux in the $CO/CH_4$ column and as refrigerant in the feed/effluent exchangers. The evaporated CO is reheated in one of the feed/effluent exchangers before recompression in the CO compressor.

The hydrogen compressor unit 148 comprises three parallel reciprocating, non-lubricated compressors which can each compress 50% of the hydrogen produced into line 152. Normally two compressors are on line and the third is a spare. The hydrogen in line 152 is sent to load up the existing ammonia plant (not shown), and the rest of the hydrogen product is used to make ammonia in a new ammonia plant (not shown)

The make-up syngas in line 125 (see FIG. 4) is more balanced for MeOH synthesis and has a lower R ratio relative to the original plant. The lower R value is due to $CO_2$ reforming and results in lower circulation in recycle line 124 and in very little purge from the MeOH loop via line 160 and valve 78. Gas from the discharge of the recycle stage 126 flows through line 162 to original methanol converter 164 and process flows essentially follow the original process flow scheme in line 166, heat recovery and cooling unit 168, line 170, methanol separator 172, recycle line 124, recycle line 104, letdown vessel 174, methanol line 178, and fuel gas stream 176, at flows less than, for example, 61-65%, of original operating flows.

During second mode operation with methanol feed to reformer 106, valve 66 on line 123, valve 68 on methanol line 178, valve 78 on line 160, and valve 80 on recycle line 104 are used to isolate the methanol synthesis loop of the original plant from the remainder of the plant. This is due to the fact that the methanol synthesis loop is shut down in second mode operation.

Example 1

Figure 7:
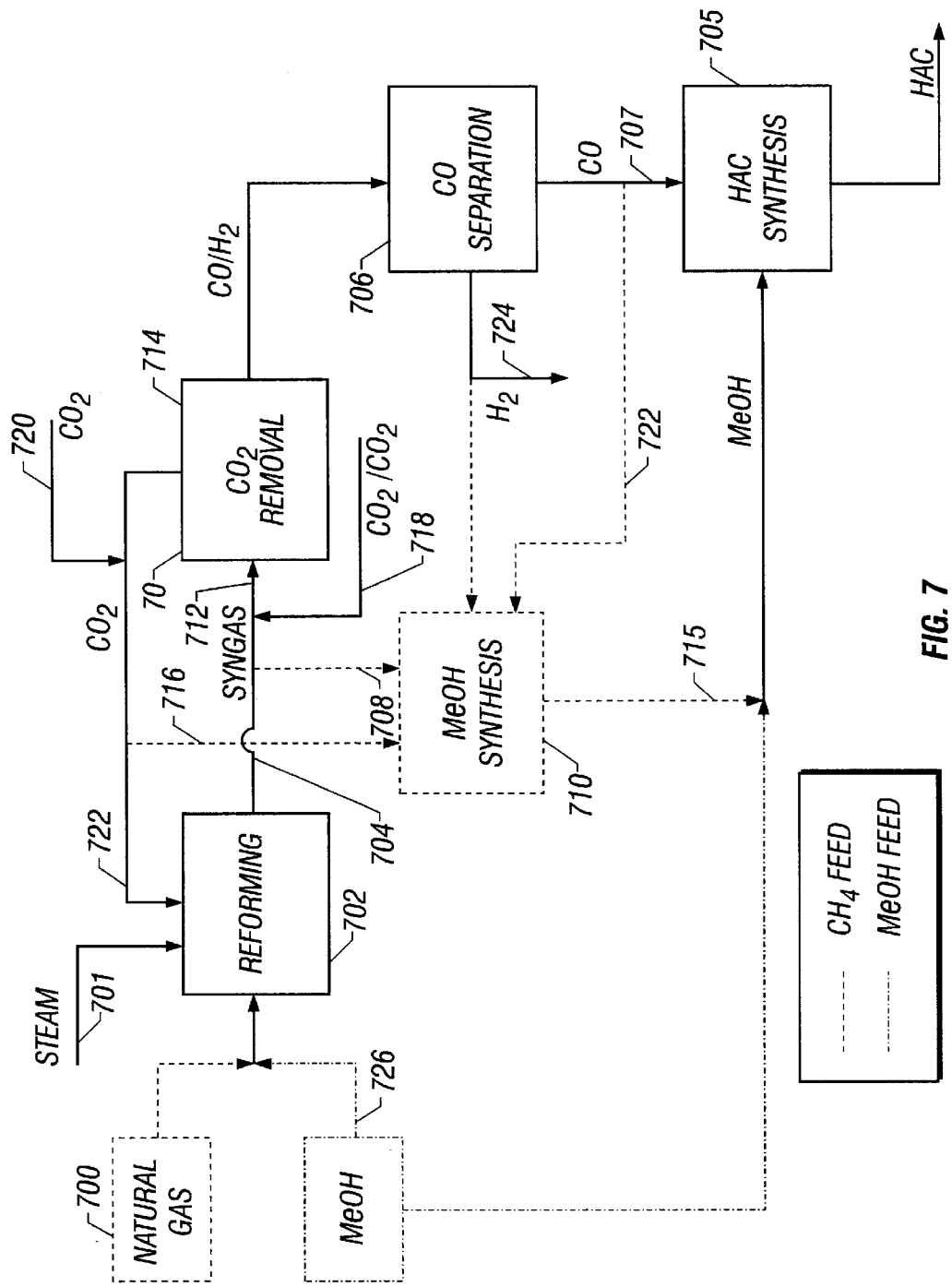
FIG. 7 is a schematic block flow diagram for a methanol plant converted for bimodal acetic acid operation based on natural gas feedstock (- - -) or imported methanol (-·-·-), with optional $CO/CO_2$ importation.

An existing methanol plant is reconfigured to produce methanol and CO in a stoichiometric ratio for the manufacture of 1,000,000 metric tons/year of acetic acid from either natural gas feedstock or MeOH, in accordance with the embodiment of FIG. 7. Assuming 340 days/year of production, this is about 2040 kmol/h of acetic acid, which requires 2040 kmol/h MeOH and 2040 kmol/h CO.

Assume the original plant converts natural gas 700 and steam 701 in two single-pass reformers 702 to form synthesis gas 704 containing about 11,660 kmol/h hydrogen, 2180 kmol/hr CO, and 1290 kmol/h $CO_2$. To produce the desired quantity of acetic acid in new reactor 705, at least enough syngas to obtain 2040 kmol/h of CO in line 707 from the new CO separation unit 706 has to be diverted from the feed 708 to the existing methanol synthesis unit 710 to the feed 712 to the new $CO_2$ removal unit 714. This leaves 140 kmol/h CO in the remaining syngas for feed 708 to the methanol synthesis unit 710. To make 2040 kmol/h MeOH for supply to reactor 705 via line 715, there is needed a total of 2040 kmol/h of any combination of CO and/or $CO_2$. With the 140 kmol/h CO from the remaining syngas in line 708, and 1290 kmol/h $CO_2$ from the remaining syngas in line 708, as well as the $CO_2$ from the $CO_2$ removal unit 714 via line 716, an additional 610 kmol/h $CO/CO_2$ is needed. This $CO/CO_2$ is imported via new $CO/CO_2$ line 718 and/or new $CO_2$ line 720, eventually supplied via line 716 and/or line 724 from the CO separator 706. Excess $CO_2$ can be recycled to the reformers 702 via line 722.

To produce the methanol in methanol synthesis unit 710 for this mode of operation, there are needed two moles of hydrogen for each mole of CO feed, as well as three moles of hydrogen for each mole of $CO_2$ feed, or, assuming the additional $CO/CO_2$ is supplied as $CO_2$, (2)(140)+(3)(1290+ 610)=5980 kmol/h $H_2$. The two existing reformers 702 produce 11,660 kmol/h, leaving 5680 kmol/h hydrogen for export via line 724.

Example 2

The same plant of Example 1 is then switched to operation in MeOH-importation mode without any $CO/CO_2$ import via lines 718 or 720. Approximately 2600 kmol/h MeOH are vaporized and fed to the reformers 702 via line 726 along with recycled $CO_2$ from the $CO_2$ removal unit 714 via line 722 and 7420 kmol/h steam via line 701 to make roughly 3360 kmol/h of recoverable $CO_2$, 2040 kmol/h recoverable CO and 5440 kmol/h hydrogen recoverable as pure hydrogen and/or fuel gas. The MeOH synthesis loop 710 is not used in this mode of operation, and instead an additional 2040 kmol/h MeOH is imported for feed to the acetic acid reactor 705 via line 728. This brings the total MEOH import to 4640 kmol/h and leaves the hydrogen produced for export or fuel gas via line 724, which is no longer needed for the MeOH synthesis, at 5440 kmol/h.

Example 3

The operation of the methanol plant of Example 2 is reconfigured for the importation of a 1038 kmol/h $CO_2$ stream via line 720, which is added to the $CO_2$ recycle stream 722. This reduces the MeOH feed 726 to the reformers 702 to about 1500 kmol/h, the steam feed 701 to 4260 kmol/h, and the recoverable hydrogen 724 to about 2400 kmol/h. The total imported MeOH is reduced to 3540 kmol/h. The radiant duty of the reformers 702 is reduced by about 16 percent, the mixed feed preheat is increased by about 38 percent, and the feed preheat decreased by about 43 percent, relative to Example 2.

Example 4

The operation of the methanol plant of Example 3 is further reconfigured for the additional importation of a 2390 kmol/h mixed stream 718 comprising approximately 30 mole percent hydrogen, 11 mole percent carbon monoxide, 45 mole percent $CO_2$, and 13 mole percent methane, which is added to the reformer effluent 712 upstream from the $CO_2$ removal unit 714. This reduces the MeOH feed 726 to the reformers 702 to about 1170 kmol/h, the steam feed 701 to 3340 kmol/h, and the recoverable hydrogen 724 to about 2400 kmol/h. The total imported MeOH is reduced to 3210 kmol/h. The radiant duty of the reformers 702 is reduced by about 22 percent, the mixed feed preheat is increased by about 47 percent, and the feed preheat decreased by about 55 percent, relative to Example 2.

What is claimed is:

1. A method for converting an original methanol plant to a converted plant having bimodal operation, the method comprising the steps of:

providing the original methanol plant having at least one steam reformer for converting a hydrocarbon to a syngas stream containing hydrogen, carbon monoxide, and carbon dioxide, and a methanol synthesis loop for converting hydrogen and carbon monoxide from the syngas stream to methanol;

providing for selectively supplying a gaseous feed to the at least one steam reformer, wherein in a first mode the gaseous feed is a hydrocarbon and in a second mode the gaseous feed is a vaporized lower alkanol;

installing a vaporizer for vaporizing a lower alkanol from an imported source into the vaporized lower alkanol;

loading the at least one steam reformer with a hydrocarbon reformation catalyst for syngas generation;

installing a separation unit for separating all or part of the syngas stream into respective streams rich in carbon dioxide, carbon monoxide and hydrogen;

providing for diverting all or part of the syngas stream originally fed to the methanol synthesis loop to the separation unit;

providing for supplying at least a portion of the carbon dioxide-rich stream to the at least one steam reformer, to the methanol synthesis loop, or to a combination thereof;

installing isolation valves for isolating the methanol synthesis loop from the remainder of the converted plant when operated in the second mode;

installing a reactor for reacting carbon-monoxide and methanol to form a product selected from the group consisting of acetic acid, acetic anhydride, methyl formate, methyl acetate and combinations thereof;

providing for supplying at least a portion of the carbon monoxide-rich stream from the separation unit to the reactor; and providing for selectively supplying a methanol stream to the reactor in the first mode from the methanol synthesis loop and in the second mode from an imported source.

2. A method for operating the converted plant of claim 1, the method comprising the steps of:

selecting between the first mode and the second mode of operation; and operating the converted plant in the selected mode, wherein the first mode of operation has at least the following steps: feeding the hydrocarbon to the at least one steam reformer, operating the at least one steam reformer to generate syngas, separating at least a portion of the syngas stream in the separation unit into respective streams rich in carbon dioxide, carbon monoxide and hydrogen, operating the methanol synthesis loop with a feed comprising (1) carbon dioxide and (2) hydrogen, reacting at least a portion of the carbon monoxide-rich stream from the separation unit with methanol from the methanol synthesis loop to form the product, and wherein the second mode of operation has at least the following steps:

vaporizing the lower alkanol, feeding the vaporized lower alkanol to the at least one steam reformer, operating the at least one steam reformer to generate syngas, separating all or part of the syngas stream in the separation unit into respective streams rich in carbon dioxide, carbon monoxide and hydrogen, isolating the methanol synthesis loop from the remainder of the converted plant, and reacting at least a portion of the carbon monoxide-rich stream from the separation unit with methanol from an imported source to form the product.

3. The method of claim 2, wherein the first mode is selected and the feed to the methanol synthesis loop comprises imported carbon dioxide.

4. The method of claim 2, wherein the first mode is selected and the feed to the methanol synthesis loop includes a portion of the syngas.

5. The method of claim 2, wherein the first mode is selected and essentially all of the syngas stream is supplied to the separation step.

6. The method of claim 2, wherein the first mode is selected and the hydrogen supplied to the methanol synthesis loop is provided by supplying at least a portion of the hydrogen-rich stream to the methanol synthesis loop.

7. The method of claim 6, wherein the first mode is selected and the amount of the hydrogen-rich stream is in excess of the stoichiometric hydrogen required by the methanol synthesis loop.

8. The method of claim 2, wherein the first mode is selected and essentially all of the carbon dioxide-rich stream is supplied to the methanol synthesis loop.

9. The method of claim 2, wherein essentially all of the carbon monoxide-rich stream is supplied to the reaction step.

10. The method of claim 2, wherein the second mode is selected.

11. The method of claim 10, wherein the lower alkanol is methanol.

12. The method of claim 2, wherein the feed to the at least one steam reformer includes a carbon dioxide-rich stream.

13. The method of claim 2, wherein the feed to the at least one steam reformer includes steam.

14. The method of claim 2, wherein the product is acetic acid.

15. The method of claim 2, wherein
the first mode is selected,
a major portion of the syngas stream is supplied to the separation unit, and
the feed of carbon dioxide and hydrogen to the methanol synthesis loop comprises at least
the carbon dioxide-rich stream from the separation unit,
a minor amount of the syngas stream, and
carbon dioxide from an additional source.

16. The method of claim 2, wherein:
the first mode is selected, all of the syngas stream is supplied to the separation unit, the feed of carbon dioxide and hydrogen to the methanol synthesis loop is selected from:
the carbon dioxide-rich stream from the separation unit,
a portion of the hydrogen-rich stream from the separation unit,
a minor portion of the syngas stream, and
carbon dioxide from an additional source, and
reacting the carbon monoxide-rich stream from the separation unit with the methanol in essentially stoichiometric proportions to form the product.

17. The process of claim 15, wherein the reaction step comprises the intermediate formation of methyl formate and isomerization of the methyl formate to acetic acid.

18. The process of claim 15, wherein the reaction step comprises the intermediate reaction of one mole of CO and two moles of methanol to form methyl acetate and hydrolysis of the methyl acetate to acetic acid and methanol.

19. A method for converting an original methanol plant into a converted plant, the method comprising the steps of:
providing an original methanol plant having at least one steam reformer for converting a hydrocarbon to a syngas stream containing hydrogen and carbon monoxide,
a heat recovery section for cooling the syngas stream,
a compression unit for compressing the syngas stream, and
a methanol synthesis loop for converting at least a portion of the hydrogen and carbon monoxide in the syngas stream to methanol;
providing for selectively supplying a gaseous feed to the at least one steam reformer, wherein in a first mode the gaseous feed is a hydrocarbon and in a second mode the gaseous feed is vaporized lower alkanol;
installing a vaporizer for vaporizing the lower alkanol from an imported source;
loading the at least one steam reformer with a hydrocarbon reformation catalyst for syngas generation;
installing a separation unit for separating the syngas fed thereto into respective streams rich in carbon dioxide, carbon monoxide and hydrogen;
installing isolation valves for isolating the methanol synthesis loop from the remainder of the converted plant when operated in the second mode;
modifying the flow of the syngas stream to allow diverting at least a portion of the syngas stream from the at least one reformer as a diverted syngas stream to the separation unit;
wherein the separation unit is configured to separate the diverted syngas stream into at least a carbon monoxide-rich stream and a hydrogen-rich stream, wherein the quantity of hydrogen in the hydrogen-rich stream is greater than any net hydrogen production of the original methanol plant;
modifying the operation of the methanol synthesis loop when in the first mode by changing the feed thereto to include at least the remaining syngas stream to produce less methanol than the original methanol plant;
installing a reactor for reacting the carbon monoxide-rich stream from the separation unit with methanol to form a product selected from the group consisting of acetic acid, acetic anhydride, methyl formate, methyl acetate and combinations thereof,
wherein when in the first mode the diversion of the syngas stream is balanced for the approximately stoichiometric production of the methanol from the methanol synthesis loop and the carbon monoxide-rich stream from the separation unit for conversion to the product;
providing for supplying at least a portion of the carbon dioxide-rich stream to the at least one steam reformer, to the methanol synthesis loop, or to a combination thereof;
providing for supplying at least a portion of the carbon monoxide-rich stream from the separation unit to the reactor; and
providing for selectively supplying methanol to the reactor in the first mode from the methanol synthesis loop and in the second mode from an imported source.

20. The method of claim 19, further comprising modifying the at least one steam reformer to increase carbon monoxide production in the syngas stream.

21. The method of claim 20, wherein the syngas stream comprises carbon dioxide and the separation unit produces a carbon dioxide-rich stream that is recycled to the at least one steam reformer to increase the carbon monoxide production.

22. The method of claims 21, wherein the syngas stream in the original plant has a molar ratio R $((H_2-CO_2)/(CO+CO_2))$ less than about 2.0 or greater than about 2.9 and wherein the syngas stream in the acetic acid plant has an R ratio from about 2.0 to about 2.9.

23. A method for converting an original methanol plant into a converted plant, the method comprising the steps of:
providing an original methanol plant having
at least one steam reformer for converting a feed comprising hydrocarbon and steam essentially free of carbon dioxide into a syngas stream containing hydrogen and carbon monoxide,
a heat recovery section for cooling the syngas stream,
a compression unit for compressing the syngas stream, and
a methanol synthesis loop for converting at least a portion of the hydrogen and carbon monoxide in the syngas stream to methanol;
providing for selectively supplying a gaseous feed to the at least one steam reformer, wherein in a first mode the gaseous feed is a hydrocarbon and in a second mode the gaseous feed is vaporized methanol from an imported source;
installing a methanol vaporizer for vaporizing the methanol to be fed to the at least one steam reformer;
loading the at least one steam reformer with a hydrocarbon reformation catalyst for syngas generation;
installing a separation unit for separating syngas into a carbon dioxide-rich stream, carbon monoxide-rich stream and a hydrogen-rich stream;
providing for diverting at least a portion of the syngas stream originally fed to the methanol synthesis loop to the separation unit;
providing for recycling at least a portion of the carbon dioxide-rich stream from the separation unit to the at least one steam reformer to increase the carbon monoxide formation relative to the original methanol plant and increase the molar ratio of carbon monoxide to hydrogen;
installing isolation valves for isolating the methanol synthesis loop from the remainder of the converted plant when operated in the second mode;
installing a reactor for reacting carbon monoxide and methanol to form a product selected from the group consisting of acetic acid, acetic anhydride, methyl formate, methyl acetate and combinations thereof;
providing for supplying at least a portion of the carbon monoxide-rich stream from the separation unit to the reactor; and
providing for selectively supplying methanol to the reactor in the first mode from the methanol synthesis loop and in the second mode from an imported source,
wherein in the first mode the diversion of the syngas stream is balanced for the approximately stoichiometric production of the methanol from the methanol synthesis loop using the remaining portion of the syngas stream and the carbon monoxide-rich stream from the separation unit for conversion to acetic acid in the reactor.

24. The method of claim 23, wherein the at least one steam reformer is modified to operate at a higher temperature.

25. The method of claim 23, wherein the separation unit comprises a solvent absorber and stripper for carbon dioxide recovery and a cryogenic distillation unit for carbon monoxide hydrogen recovery.

26. The method of claim 23, Wherein the compression unit comprises a three-stage compressor and the syngas stream diversion occurs between the second and third compression stages.

27. The method of claim 26, further comprising modifying the third compressor stage for operation at lower throughput than the original methanol plant.

28. The method of claim 23, wherein the methanol synthesis loop of the original methanol plant comprises a recycle loop compressor, wherein the recycle loop compressor is modified for operation at a lower throughput.

29. A method for converting an original methanol plant to a converted plant, the method comprising the steps of:
providing the original methanol plant having
at least one steam reformer for converting a hydrocarbon to a syngas stream containing hydrogen, carbon monoxide, and carbon dioxide, and
a methanol synthesis loop for converting hydrogen and carbon monoxide from the syngas stream to methanol;
providing for supplying a gaseous feed to the at least one steam reformer, wherein the gaseous feed is a vaporized lower alkanol;
installing a vaporizer for vaporizing a lower alkanol from an imported source into the vaporized lower alkanol;
loading the at least one steam reformer with a hydrocarbon reformation catalyst for syngas generation;
installing a separation unit for separating all or part of the syngas stream into respective streams rich in carbon dioxide, carbon monoxide and hydrogen;
providing for diverting all of the syngas stream originally fed to the methanol synthesis loop to the separation unit;
providing for supplying at least a portion of the carbon dioxide-rich stream to the at least one steam reformer;
installing isolation valves for isolating the methanol synthesis loop from the remainder of the converted plant;
installing a reactor for reacting carbon monoxide and methanol to form a product selected from the group consisting of acetic acid, acetic anhydride, methyl formate, methyl acetate and combinations thereof;
providing for supplying at least a portion of the carbon monoxide-rich stream from the separation unit to the reactor; and
providing for supplying a methanol stream from an imported source.

30. A method for operating the converted plant of claim 29, the method comprising the steps of:
vaporizing the lower alkanol, feeding the vaporized lower alkanol to the at least one steam reformer,
operating the at least one steam reformer to generate syngas,
separating all or part of the syngas stream in the separation unit into respective streams rich in carbon dioxide, carbon monoxide and hydrogen,
isolating the methanol synthesis loop from the remainder of the converted plant, and
reacting at least a portion of the carbon monoxide-rich stream from the separation unit with methanol from an imported source to form the product.

31. The method of claim 30, wherein the lower alkanol is methanol.

32. The method of claim 30, wherein the product is acetic acid.

* * * * *